(12) United States Patent
Shapiro et al.

(10) Patent No.: US 6,630,175 B1
(45) Date of Patent: Oct. 7, 2003

(54) METHOD OF REDUCING EYE IRRITATION

(75) Inventors: Stanley S. Shapiro, Livingston, NJ (US); Benjamin C. Wiegand, Newtown, PA (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/607,118

(22) Filed: Jun. 29, 2000

(51) Int. Cl.$^7$ ................... A01N 59/06; A01N 59/02; A61K 33/06; A61K 33/04
(52) U.S. Cl. ........................... 424/682; 424/709
(58) Field of Search .................. 424/600, 682, 424/709

(56) References Cited

U.S. PATENT DOCUMENTS

| | | |
|---|---|---|
| 4,320,145 A | 3/1982 | Cavazza |
| 4,961,927 A * | 10/1990 | Kogure ................. 424/94.3 |
| 5,106,624 A | 4/1992 | Bertini |
| 5,376,379 A | 12/1994 | Fabre et al. |
| 5,531,993 A | 7/1996 | Griat |
| 5,536,751 A | 7/1996 | Bunger |
| 5,578,312 A | 11/1996 | Parrinello |
| 5,627,212 A | 5/1997 | Cavazza et al. |
| 5,637,305 A | 6/1997 | Cavazza et al. |
| 5,641,814 A | 6/1997 | Martin |
| 5,690,946 A | 11/1997 | Koulbanis et al. |
| 5,756,107 A | 5/1998 | Hahn et al. |
| 5,759,610 A | 6/1998 | Nishimoto et al. |
| 5,821,237 A | 10/1998 | Bissett et al. |
| 5,928,657 A | 7/1999 | Simon |
| 5,932,234 A | 8/1999 | Simon et al. |
| 5,935,636 A | 8/1999 | Nishimoto et al. |
| 5,951,990 A | 9/1999 | Ptchelintsev |
| 5,997,885 A | 12/1999 | Koulbanis et al. |
| 6,033,684 A | 3/2000 | Norcia |
| 6,106,846 A | 8/2000 | Breton et al. |

FOREIGN PATENT DOCUMENTS

| | | |
|---|---|---|
| EP | 0 413 528 A1 | 2/1991 |
| EP | 0 573 465 B1 | 12/1993 |
| EP | 0 600 730 B1 | 6/1994 |
| EP | 0273202 B1 | 6/1995 |
| EP | 0 711 543 A1 | 5/1996 |
| EP | 0 717 984 A2 | 6/1996 |
| EP | 0 868 916 A2 | 10/1998 |
| EP | 0 974 342 A1 | 1/2000 |
| EP | 0 983 727 A2 | 3/2000 |
| EP | 0 998 914 A1 | 5/2000 |
| FR | 1248192 | 1/1960 |
| FR | 3574 M | 5/1964 |
| FR | 2627385 | 8/1989 |
| FR | 2619007 | 2/1999 |
| GB | 0559502 | 3/1996 |
| GB | 0699432 | 1/1997 |
| GB | 0773012 | 11/1997 |
| GB | 0846462 | 12/1999 |
| JP | 62122671 * | 6/1987 |
| WO | WO 84/04885 A1 | 12/1984 |
| WO | WO 89/06958 A1 | 8/1989 |
| WO | WO 95/03028 A1 | 2/1995 |
| WO | WO 95/04537 A1 | 2/1995 |
| WO | WO 95/13793 A1 | 5/1995 |
| WO | WO 95/27501 A1 | 10/1995 |
| WO | WO 96/11572 A1 | 4/1996 |
| WO | WO 97/15282 A1 | 5/1997 |
| WO | 99/07388 A1 | 7/1998 |
| WO | 99/08681 A1 | 8/1998 |
| WO | WO 98/51277 A1 | 11/1998 |
| WO | WO 00/04870 A2 | 2/2000 |

OTHER PUBLICATIONS

Evian Moisture Cream package and translation.
Evian Moisture Lotion Gentle product bottle and translation.
Evian Oil Free Skin Lotion product bottle and translation.
Evian Washing Cream product tube and translation.
Evian Moisture Cream product jar and translation.
Evian packaging insert for Evian Washing Cream, Skin Lotion and Moisture Lotion.
Medical Guide to the Mineral Waters of France and its Wintering Stations, A. Vintras, M.D., 1883, J&A Churchill, London, pp. 261–263.
Balsom, P. Soderlund, K. and Ekbom, B., Creatine in Humans with Special Reference t Creatine Supplementation, Sports Med. 1994, 268–280, 18 (4).
Bremer, J., Carnitine–Metabolism and Functions, Physiological Reviews, 1983, 1420–1480, vol. 63 No. 4.
Stanko, R., Tietze, D and Arch, Body Compositin, energy utilization, and nitrogen metabolism with a 4.25–MJ/d low–energy diet supplemented, American Journal Clinical Nutr. 1992, 630–635, vol. 56 (4).
Evian "Le brumisateur®", S.A. des Eaux Minerales d'Evian, excerpt taken from Water . . . It's Life., Evian publication dated May, 1997.
EPO Search Report dated Nov. 17, 2000 for patent application No. 00307059.6.
U.S. patent application Ser. No. 09/606,490, Johnson & Johnson Consumer Companies, Inc., pending.
U.S. patent application Ser. No. 09/607,557, Johnson & Johnson Consumer Companies, Inc., pending.
U.S. patent application Ser. No. 09/606,889, Johnson & Johnson Consumer Companies, Inc., pending.
U.S. patent application Ser. No. 09/606,556, Johnson & Johnson Consumer Companies, Inc., pending.
U.S. patent application Ser. No. 09/606,491, Johnson & Johnson Consumer Companies, Inc., pending.
Abstract of JP 51148042 publication date Dec. 17, 1976.
EPO Search Report dated Jul. 23, 2001 for Patent Application No. 00 307 059.6–2114.

* cited by examiner

*Primary Examiner*—Alton N. Pryor
(74) *Attorney, Agent, or Firm*—WIlliam E. McGowan

(57) ABSTRACT

The present invention relates to method of reducing eye irritation caused by a cosmetic composition comprising incorporating a reducing amount of mineral water into said cosmetic composition.

21 Claims, No Drawings

METHOD OF REDUCING EYE IRRITATION

FIELD OF THE INVENTION

The present invention relates to a method of reducing eye irritation in cosmetic compositions.

BACKGROUND OF THE INVENTION

Cosmetics, such as facial moisturizing creams and lotions, sunscreen compositions, and shampoos are often applied near the eye. These compositions can come into contact with the eye either during application, following subsequent rubbing of around the eye, or as a result of perspiration. As the eye only has an epithelial barrier, it is more sensitive to cosmetic compositions than the skin, which possesses both a stratum corneum and epidermal barrier layers. Thus, compositions that are otherwise non-irritating to the skin can often irritate, e.g., sting, the eye.

The present invention relates to a method of reducing eye irritation in cosmetic compositions by adding mineral water, e.g., in place of some or all of the distilled water.

SUMMARY OF THE INVENTION

The invention features a method of reducing eye irritation such eye redness (e.g., the appearance of blood vessles in the eye) or eye sting (e.g., pain in the eye), caused by a cosmetic composition, comprising incorporating a reducing amount of mineral water into the cosmetic composition. In one embodiment, the method reduces the eye irritation, sting, or redness of the composition by at least about 5% such as at least about 20%.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to a method of reducing eye irritation caused by a cosmetic composition comprising incorporating mineral water into said cosmetic composition.

What is meant by mineral water is water having mineralization (i.e., the sum of the concentrations of anions and cations present in the water) of at least about 200 mg/L (e.g., at least about 300 mg/L such from about 400 mg/L to about 1000 mg/L). Examples of such anions and cations include, but are not limited to, calcium, magnesium, bicarbonates, sulfates, potassium, sodium, chlorides, nitrates, phosphates, lithium, manganese, sulfites, fluoride, and iodide. In one embodiment, the mineral water has at least about 5 mg/L, e.g., at least about 10 mg/L, of magnesium and at least about 10 mg/L of calcium, e.g., at least about 20 mg/L.

The mineral water may be a naturally mineralized water, e.g., a mineral water suitable for consumption, or a thermal spring water, which is often not consumable. Examples of mineral water include, but are not limited to, eau d'Evian (Evian Eau Minerale Naturelle or Evian® Natural Spring Water referred herein as Evian® Mineral Water), eau Volvic, and eaux de Vittel (e.g., Grande Spring or Hepar Spring). Examples of thermal spring waters include eau de la Bourboule, eau d'Enghien-les-bains, eau d'Allevard-les-bains, eau de Digne, eau des Maizieres, eau de Nyrac-les-bains, eau de Lons le Saunier, Eaux Bonnes, eau de Rochefort, eau de Saint Christau, eau des Fumades, eau de Tereau de. Vittel, eaux du bassin de Vichy, eau d'Uriage, eau d'Avene, and eau de la Roche Posay.

In one embodiment, the mineral water comprises (a) from about 30 mg/L to about 150 mg/L of calcium; (b) from about 10 mg/L to about 50 mg/L of magnesium; (c) from about 150 mg/L to about 700 mg/L of bicarbonates; (d) from about 0.1 mg/L to about 5 mg/L of potassium; (e) from about 1 to about 20 mg/L of sulfates; (f) from about 1 to about 10 mg/L of sodium; (g) from about 1 mg/L to about 10 mg/L of chlorides; and (h) from about 1 mg/L to about 10 mg/L of nitrates.

In one embodiment, the mineral water is Evian® Mineral Water that comprises: (a) about 78 mg/L of calcium; (b) about 24 mg/L of magnesium, (c) about 357 mg/L of bicarbonates; (d) about 1 mg/L of potassium; (e) about 10 mg/L of) sulfates; (f) about 5 mg/L of sodium, (g) about 4 mg/L of chlorides; and (h) from about 1 to about 4 mg/L nitrates.

What is meant by a reducing amount of mineral water is an amount capable of reducing the undesired effect of the composition (e.g., eye irritation, redness, or a sting). In one embodiment, the composition comprises at least about 1%, by weight, of mineral water, e.g. about 10% to about 99%, by weight, of mineral water.

The compositions of the present invention may further comprise one or more of the following compounds: creatine, carnitine, or pyruvic acid, or a cosmetically acceptable salt or ester thereof. What is meant by cosmetically acceptable salt or ester is one that does not eliminate the therapeutic benefit of the compound (e.g., its hydrating, nourishing, metabolic enhancing properties). Examples of cosmetically acceptable salts, include, but are not limited to, those with cosmetically acceptable organic acids (e.g., acetic, lactic, maleic, citric, malic, ascorbic, succinic, benzoic, methesulfonic, toluenesulfonic, or pamoic acid), as well as polymeric acids (e.g., tannic or carboxymethyl cellulose) and salts with inorganic acids such as a hydrohalic acid (e.g., hydrochloric acid, sulfuric acid, or phosphoric acid). Examples of cosmetically acceptable esters include, but are not limited to, C2–C6 alkyl esters such as methyl esters and ethyl esters. Examples of such compounds include, but are not limited to, creatine monohydrate, creatine hemisulfate, D-carnitine, L-carnitine, L-carnitine hydrochloride, sodium pyruvate, and pyruvic acid methyl ester. As used herein, if the stereochemistry of the compound is not indicated, then the compound includes all stereoisomers, if any.

The amount of carnitine or a cosmetically acceptable salt or ester thereof, creatine or a cosmetically acceptable salt or ester thereof, or pyruvic acid or a cosmetically acceptable salt or ester thereof, in the composition varies (e.g., depending on the intended use or the form of the composition) being administered and will typically be present in the composition in an amount from about 0.001% to about 10%, by weight, of the topically applied composition, e.g., from about 0.01% to about 5%, by weight, such as from about 0.01% to about 1%, by weight, of such carnitine, creatine, pyruvic acid or cosmetically acceptable salt or ester thereof.

In one embodiment, the method further comprises administering (e.g., in a composition) another cosmetically active agent. What is meant by a "cosmetically active agent" is a compound that has a cosmetic or therapeutic effect on the skin, e.g., agents to treat wrinkles, acne, or to lighten the skin. In one embodiment, the agent is selected from, but not limited to the group consisting of hydroxy acids, benzoyl peroxide, sulfur resorcinol, ascorbic acid, D-panthenol, hydroquinone, sunscreen agents, anti-inflammatory agents, skin lightening agents, antimicrobial and antifungal agents, estrogens, 2-dimethylaminoethanol, lipoic acid, amino acids such a proline and tyrosine, lactobionic acid, acetyl-coenzyme A, niacin, riboflavin, thiamin, ribose, electron transporters such as NADH and FADH2, botanical extracts such as aloe vera and soy, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of hydroxy acids include, but are not limited to, (i) alpha-hydroxy acids such as glycolic acid, lactic acid, malic acid, citric acid, and tartaric acid, (ii) beta-hydroxy acids such as salicylic acid, and/or (iii) polyhydroxy acids. See, e.g., European Patent Application No. 273,202.

Examples of derivatives of ascorbic acid include, but are not limited to, ascorbyl palmitate, magnesium ascorbyl phosphate, sodium ascorbyl phosphate, zinc ascorbyl phosphate, ascorbyl glucoside, sodium ascorbate, and ascorbyl polypeptide. An example of a derivative of hydroquinone includes, but is not limited to, arbutin.

The method of the present invention can be practiced by topically administering to a mammal, e.g., by the direct laying on the skin or hair of a human, a composition contains the mineral water. The compositions (e.g., cosmetic compositions) useful in the subject invention involve formulations suitable for topical application to mammalian skin, the formulation comprising (i) mineral water, (ii) optionally, a safe and effective amount of the creatine, carnitine, or pyruvic acid, or a cosmetically acceptable salt or ester thereof or another cosmetically active agent(s), and (iii) optionally, a cosmetically-acceptable topical carrier. The term "cosmetically-acceptable topical carrier" refers to a carrier for topical use that is capable of having the mineral water and any other agents dispersed or dissolved therein, and possessing acceptable safety properties. In one embodiment, the cosmetically-acceptable carrier comprises mineral water (e.g., an emulsion where the aqueous phase comprises mineral water or a mineral water based cleanser or spray).

The topical compositions useful in the present invention may be used for a variety of cosmetic uses, including, but not limited to, treating, cleansing, beautifying, or covering the skin or hair of a human. The compositions, thus, may be made into a wide variety of product types. These include, but are not limited to cleansers (e.g., facial scrubs), shampoos, lotions, creams, gels, sticks, sprays, ointments, pastes, mousses, shampoos, cosmetics, and dermal patches. Examples include lip balms, moisturizing and sunscreen lotions/creams, skin cleansing compositions, and body mists. These products may comprise several types of carrier systems including, but not limited to single phase solutions (e.g., water/mineral water or oil based solutions), emulsions, and gels.

The topical compositions useful in the present invention formulated as solutions typically include a cosmetically acceptable aqueous (e.g., mineral water) and/or organic carriers (e.g., from about 80% to about 99.99%, by weight of the composition, such as from about 90% to about 99%, by weight of the composition, of an acceptable aqueous or organic solvent). Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, butanetriol, sorbitol esters, 1,2,6-hexanetriol, butanediol, and mixtures thereof.

If the topical solution useful in the present invention are formulated as an aerosol and applied to the skin as a spray-on, a propellant is added to a solution composition. Examples of propellants useful herein include, but are not limited to, chlorinated, fluorinated, and chloro-fluorinated lower molecular weight hydrocarbons. Other propellants useful herein can be found in Sagafin, Cosmetics Science and Technology, 2nd Edition, Vol. 2, pp. 443–65 (1972) (hereinafter "Sagafin") and the ICI Handbook pp. 1655.

A lotion can be made from a solution carrier system. Lotions typically comprise from about 1% to about 20% by weight of the composition (e.g., from about 5% to about 10%) of an emollient(s) and from about 50% to about 90% by weight of the composition (e.g., from about 60% to about 80%) of water (e.g., mineral water).

Another type of product that may be formulated from a solution carrier system is a cream. A cream typically comprises from about 5% to about 50% by weight of the composition (e.g., from about 10% to about 20%) of an emollient(s) and from about 45% to about 85% by weight of the composition (e.g., from about 50% to about 75%) of water (e.g., mineral water).

Yet another type of product that may be formulated from a solution carrier system is an ointment. An ointment may comprise a simple base of animal or vegetable oils or semi-solid hydrocarbons. Ointments may also comprise absorption ointment bases that absorb water to form emulsions. Ointment carriers may also be water-soluble. An ointment may comprise from about 1% to about 20% by weight of the composition of an emollient(s) plus from about 0.1% to about 2% by weight of the composition of a thickening agent(s). A more complete disclosure of thickening agents or viscosity increasing agents useful herein can be found in Sagafin pp. 72–73 and the ICI Handbook pp. 1693–97.

If the carrier is formulated as an emulsion (e.g., an oil-in-water, silicone-in-water, water-in-oil, or water-in-silicone emulsion), from about 1% to about 10% by weight of the composition (e.g., from about 2% to about 5%) of the carrier system may comprise an emulsifier(s). Emulsifiers may be nonionic, anionic, cationic, or zwitterionic. Suitable emulsifiers are disclosed in, for example, U.S. Pat. No. 3,755,560, U.S. Pat. No. 4,421,769, McCutcheon's Detergents and Emulsifiers, North American Edition, pp. 317–24 (1986), and the ICI Handbook, pp.1673–86.

Lotions and creams can also be formulated as emulsions. Typically, such emulsions may comprise from 0.5% to about 5% by weight of the composition of an emulsifier(s). Creams may typically comprise from about 1% to about 20% by weight of the composition (e.g., from about 5% to about 10%) of an emollient(s); from about 20% to about 80% by weight of the composition (e.g., from about 30% to about 70%) of water (e.g., mineral water); and from about 1% to about 10% by weight of the composition (e.g., from about 2% to about 5%) of an emulsifier(s).

Two phase emulsion skin care preparations, such as lotions and creams, of the oil-in-water type and water-in-oil type are well-known in the cosmetic art and are useful in the subject invention. Triphase emulsion compositions, such as the water-in-oil-in-water type, as disclosed in U.S. Pat. No. 4,254,105, are also useful in the subject invention. In general, such triphase emulsions contain water, emollients, and emulsifiers as essential ingredients. Triple emulsion carrier systems comprising an oil-in-water-in-silicone fluid emulsion composition, as disclosed in U.S. Pat. No. 4,960, 764, may also be useful in the subject invention.

The methods of the present invention may also comprise administering a composition containing one or more of the following: antioxidants (e.g., ascorbic acid, tocopherols, polyphenols, tocotrienols, BHA, and BHT), chelating agents (e.g., EDTA), and preservatives (e.g., parabens). Examples of suitable antioxidants, preservatives, and chelating agents are listed in pp. 1612–13, 1626, and 1654–55 of the ICI Handbook. In addition, the topical compositions useful herein can contain conventional cosmetic adjuvants, such as dyes, opacifiers (e.g., titanium dioxide), pigments, and fragrances.

The compositions and cosmetic formulations for use in the methods of the present invention may be prepared using methodology that is well known by an artisan of ordinary skill. The following is a description of the testing and manufacturing of cosmetic compositions of the present invention.

EXAMPLE 1

Mineral Water Containing Carnitine, Trehalose, and Sodium Pyruvate

A composition containing Evian® Mineral Water (Evian, France), carnitine, sodium pyruvate, and trehalose was manufactured using the ingredients listed in Table I.

TABLE I

| INGREDIENTS | % Weight |
|---|---|
| L-Carnitine | 1 |
| Sodium Pyruvate | 1 |
| Trehalose | 1 |
| D-Panthenol (75%)/Water (25%) | 1.3 |
| Magnesium Ascorbyl Phosphate | 1 |
| L-Proline | 1 |
| Mineral Water | 72.7 |
| Pentylene Glycol | 20 |
| Phenoxyethanol | 1 |

The mineral water was first heated to 30° C. The other ingredients were then added and dissolved one by one under mixing conditions. The pentylene glycol was obtained from Dragoco Gerberding & Co. (Holzminden, Germany) under the tradename Hydrolite®-5.

EXAMPLE 2

Skin Cleansing Emulsion

A skin cleansing emulsion composition containing the composition of Example 1 was manufactured using the ingredients listed in Table II.

TABLE II

| INGREDIENTS | % WEIGHT |
|---|---|
| Oil Phase Ingredients | |
| Isononyl Isononanoate | 2 |
| Cyclomethicone | 2 |
| Isostearyl Palmitate | 2 |
| Cetyl Octanoate | 2 |

TABLE II-continued

| INGREDIENTS | % WEIGHT |
|---|---|
| Pentaerythritol Tetraoctanoate | 2 |
| Tocopheryl Acetate | 0.01 |
| Evening Primrose Oil | 0.01 |
| Water Phase Ingredients | |
| Mineral Water | q.s. 100 |
| Carbomer | 0.5 |
| Hexylene Glycol | 1 |
| Sucrose Cocoate | 0.4875 |
| Methyl paraben | 0.4 |
| Propyl paraben | 0.1 |
| Disodium EDTA | 0.1 |
| Neutralization Ingredient | |
| 20% Sodium Hydroxide | 0.1360 |
| Post Addition Ingredient | |
| Arnica Montana Extract 5–10%/Propylene Glycol 40–70%/water 25–50% | 0.1 |
| Sodium Pyruvate | 0.04 |
| Peg-6 Caprylic-capric Glycerides | 0.75 |
| Composition of Example 1 | 1 |
| Fragrance | 0.05 |

The mineral water (Evian® Mineral Water, Evian, France) and the disodium EDTA were heated to 85° C., and heat was maintained for about 15 min. The carbomer (Carbopol Ultrez® 10 from BF Goodrich Performance Materials, Consumer Specialties Group, Cleveland Ohio) was slowly added to the mixture and mixed for about 20 min. The mixture was then cooled to 65° C., following which the Peg-6 caprylic-capric glycerides (Tegosoft® GMC6 from Tegasoft Co., Th Goldschmit AG, Essen, Germany), sucrose cocoate, hexylene glycol, methyl paraben, and propyl paraben were added. In a separate beaker, the Oil Phase Ingredients were mixed and heated to 60° C. (with the tocopheryl acetate and evening primrose oil being added just before mixing with the mixture in the first beaker). The mixture of the second beaker was added to the water phase and mixed for about 15 min. The mixture was then neutralized with the 20% sodium hydroxide aqueous solution and mixed until uniform. The mixture was then cooled to 35° C., and the sodium pyruvate, carnitine, Arnica Montana Extract/Propylene Glycol/Water (Vegetol Arnica MCF 115 Hydro® from Gattefosse SA, Saint Priest Cedex, France), and the composition of Example 1 were added. Finally, the fragrance was then added to the resulting mixture.

EXAMPLE 3

Reduction of Ocular Irritation with Compositions Containing Mineral Water

The ocular irritation potential of products, with or without mineral water, were evaluated by determining their effect on the permeability of a cell layer, as assessed by the leakage of fluorescein through the layer. This method was developed as an alternative to the rabbit eye test, and is reported in Tchao, R. (1988) Trans-epithelial Permeability of Fluorescein In Vitro as an Assay to Determine Eye Irritants. Alternative Methods in Toxicology 6, Progress in In Vitro Toxicology (ed. A. M. Goldberg), 271.

Damage to the permeability barrier is quantified by measuring the amount of marker dye, sodium fluorescein, which leaked across a layer of MDCK cells grown on a microporous filter, to the lower well. Damage is assessed over a range of test composition concentrations. The amount of dye leakage following exposure to each concentration is determined spectrophotometrically by measuring the optical density (490 nm).

Reduction of ocular irritation was measured in the following six different products- (i) the composition of Example 2, (ii) the composition of Example 2 wherein the mineral water was replaced with distilled water; (iii) a composition of Example 3; (iv) the same composition of Example 2 except that the mineral water was replaced with distilled water; (v) Johnson's Baby Shampoos ("JBS") (Johnson & Johnson Consumer Companies, Inc., Skillman, N.J.); and (vi) Johnson's Baby Shampoo except that the mineral water was replaced with distilled water. For JBS and the composition of Example 2, leakage was plotted against concentration, and a mean $EC_{50}$ value was determined by probit analysis as set forth in the Table III.

TABLE III

| Composition | $EC_{50}$ |
| --- | --- |
| JBS (Distilled Water) | 3.13 ± 0.95 |
| JBS (Mineral Water) | 5.74 ± 1.5 |
| Example 2 (Distilled Water) | 3.11 ± 0.86 |
| Example 2 (Mineral Water) | 3.62 ± 0.56 |

The use of mineral water in the JBS composition was surprisingly found to result in 45% increase in the EC50 of the two JBS compositions, thus indicating that almost twice as much of the JBS formulation can be administered to the eye when mineral water is used in place of distilled water. An increase in EC50 was also seen with the compositions of Example 3.

For the composition of Example 2, the formulations with either distilled water or mineral water were both mild, so optical density at full concentration was measured as set forth in Table IV.

TABLE IV

| Composition | % of Maximum Leakage |
| --- | --- |
| Example 2 (Distilled Water) | 56 |
| Example 2 (Mineral Water) | 48 |

The above data in Table IV shows that there is less leakage of sodium fluorescein when the formulation was manufactured with mineral water rather than distilled water.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of reducing eye irritation caused by a cosmetic composition, said method comprising incorporating a reducing amount of natural mineral water into said cosmetic composition that is topically administer to skin or hair, wherein said mineral water comprises from about 10 to about 150 mg/L of calcium, from about 5 to about 50 mg/L of magnesium, and from about 1 to about 20 mg/L of sulphates; wherein said composition is a lip balm, skin cleansing composition, moisturizing lotion, moisturizing cream, sunscreen lotion, or sunscreen cream.

2. A method of claim 1, wherein said mineral water comprises (a) from about 30 mg/L to about 150 mg/L of calcium; (b) from about 10 mg/L to about 50 mg/L of magnesium; (c) from about 150 mg/L to about 700 mg/L of bicarbonates; and (d) from about 0.1 rag/L to about 5 mg/L of potassium.

3. A method of claim 2, wherein said mineral water further comprises (f) from about 1 to about 10 mg/L of sodium; (g) from about 1 mg/L to about 10 mg/L of chlorides; and (h) from about 1 mg/L to about 10 mg/L of nitrates.

4. A method of claim 1, wherein said mineral water comprises (a) about 78 mg/L of calcium, (b) about 24 mg/L of magnesium; (c) about 357 mg/L of bicarbonates; (d) about 1 mg/L of potassium; (e) about 10 mg/L of sulphates; (f) about 5mg/L of sodium; (g) about 4 mg/L of chlorides; and (h) about 4 mg/L nitrates.

5. A method of claim 1, wherein said mineral water is from Evian, France.

6. A method of claim 1, wherein said composition is a skin cleansing composition.

7. A method of claim 5, wherein said composition is a skin cleansing composition.

8. A method of reducing eye redness caused by a cosmetic composition, said method comprising incorporating a reducing amount of natural mineral water into said cosmetic composition that is topically administered to skin or hair, wherein said mineral water comprises from about 10 to about 150 mg/L of calcium, from about 5 to about 50 mg/L of magnesium, and from about 1 to about 20 mg/L of sulphates; wherein said composition is a lip balm, skin cleansing composition, moisturizing lotion, moisturizing cream, sunscreen lotion, or sunscreen cream.

9. A method of claim 8, wherein said mineral water comprises (a) from about 30 mg/L to about 150 mg/L of calcium; (b) from about 10 mg/L to about 50 mg/L of magnesium; (c) from about 150 mg/L to about 700 mg/L of bicarbonates; and (d) about 0.1 mg/L to about 5 mg/L of potassium.

10. A method of claim 9, wherein said mineral water further comprises (f) from about 1 to about 10 mg/L of sodium; (g) from about 1 mg/L to about 10 mg/L of chlorides; and (h) from about 1 mg/L to about 10 mg/L of nitrates.

11. A method of claim 8, wherein said mineral water comprises (a) about 78 mg/L of calcium; (b) about 24 mg/L of magnesium; (c) about 357 mg/L of bicarbonates; (d) about 1 mg/L of potassium; (e) about 10 mg/L of sulphates; (f) about 5 mg/L of sodium; (g) about 4 mg/L of chlorides; and (h) from about 4 mg/L nitrates.

12. A method of claim 8, wherein said mineral water is from Evian, France.

13. A method of claim 8, wherein said composition is a skin cleansing composition.

14. A method of claim 12, wherein said composition is a skin cleansing composition.

15. A method of reducing eye sting caused by a cosmetic composition, said method comprising incorporating a reducing amount of natural mineral water into said cosmetic composition that is topically administered to skin or hair, wherein said mineral water comprises from about 10 to about 150 mg/L of calcium, from about 5 to about 50 mg/L of magnesium, and from about 1 to about 20 mg/L of sulphates; wherein said composition is a lip balm, skin cleansing composition, moisturizing lotion, moisturizing cream, sunscreen lotion, or sunscreen cream.

16. A method of claim 15, wherein said mineral water comprises (a) from about 30 mg/L to about 150 mg/L of calcium; (b) from about 10 mg/L to about 50 mg/L of magnesium; (c) from about 150 mg/L to about 700 mg/L of bicarbonates; and (d) from about 0.1 mg/L to about 5 mg/L of potassium.

17. A method of claim 16, wherein said mineral water further comprises (f) from about 1 to about 10 mg/L of sodium; (g) from about 1 mg/L to about 10 mg/L of chlorides; and (h) from about 1 mg/L to about 10 mg/L of nitrates.

18. A method of claim 15, wherein said mineral water comprises (a) about 78 mg/L of calcium; (b) about 24 mg/L of magnesium; (c) about 357 mg/L of bicarbonates; (d) about 1 mg/L of potassium; (e) about 10 mg/L of sulphates; (f) about 5 mg/L of sodium; (g) about 4 mg/L of chlorides; and (h) about 4 mg/L nitrates.

19. A method of claim 9, wherein said mineral water is from Evian, France.

20. A method of claim 15, wherein said composition is a skin cleansing composition.

21. A method of claim 19, wherein said composition is a skin cleansing composition.

* * * * *